United States Patent [19]

Tseng et al.

[11] Patent Number: 4,904,658
[45] Date of Patent: Feb. 27, 1990

[54] SUBSTITUTED-6H,8H-PYRIMIDO-[1,2,3-CD]PURINE-8,10-(9H)-DIONES AND SUBSTITUTED-6H,10H-PYRIMIDO[1,2-CD]PURIN-10-ONES

[75] Inventors: Shin S. Tseng, Bridgewater, N.J.; Joseph W. Epstein, Monroe; Jeremy I. Levin, Spring Valley, both of N.Y.

[73] Assignee: American Cyanamid Company, Wayne, N.J.

[21] Appl. No.: 181,845

[22] Filed: Apr. 15, 1988

[51] Int. Cl.$^4$ .................. A61K 31/505; C07D 487/16
[52] U.S. Cl. .................. 514/233.2; 514/267; 544/115; 544/251
[58] Field of Search ............ 544/251, 115; 514/267, 514/233.2

[56] References Cited

U.S. PATENT DOCUMENTS 4,236,005  11/1980  Dusza et al. .................. 544/281
4,663,326   5/1987  Hamilton ...................... 514/258
4,680,295   7/1987  Fowler et al. ................. 514/258

OTHER PUBLICATIONS

Leonard et al., Chemical Abstracts, vol. 65:17264g, (1966).
Seden et al., Chemical Abstracts, vol. 84:59392s, (1976).
Holy, Chemical Abstracts, vol. 96:181605b, (1982), also attached subjects Index page.
Kim et al., Chemical Abstracts, vol. 109:128973f, (1988), see attached CAS ONLINE search pages.
Crook et al., ed., "Assessment in Geriatric Psychopharmacology", Mark Powley Associates, Inc., (1983), pp. 263–269.

*Primary Examiner*—Mukund J. Shah
*Assistant Examiner*—Diana G. Rivers
*Attorney, Agent, or Firm*—Kenneth J. Dow

[57] ABSTRACT

Substituted-6H,8H-pyrimido[1,2,3-cd]purine-8,10(9H)-diones and substituted-6H,10H-pyrimido[1,2-cd]purin-10-ones which are useful as cognition enhancing agents, anxiolytic agents and/or antihypertensive agents in the treatment of cognitive and relative neutral behavioral problems, anxiety and hypertension in mammals.

17 Claims, No Drawings

SUBSTITUTED-6H,8H-PYRIMIDO-[1,2,3-CD]PURINE-8,10-(9H)-DIONES AND SUBSTITUTED-6H,10H-PYRIMIDO[1,2-CD]PURIN-10-ONES

BRIEF SUMMARY OF THE INVENTION

The present invention relates to new organic compounds and more particularly is concerned with novel substituted-6H,8H-pyrimido[1,2,3-cd]-purine-8,10(9H)-diones and substituted-6H,10H-pyrimido[1,2-cd]purin-10-ones useful as cognition enhancing agents, anxiolytic agents and/or antihypertensive agents in mammals. The compounds of the present invention may be represented by the following structural formula:

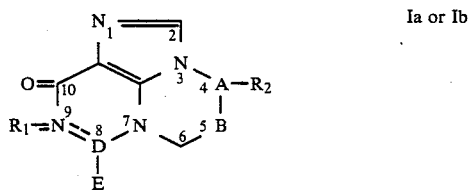

Ia or Ib wherein ---- may represent the presence of a double bond between the $C_8$ and $C_9$ position, structure Ia or the absence of a double bond between the $C_8$ and $C_9$ position, structure Ib, and where in structure Ia or Ib A—B may be either

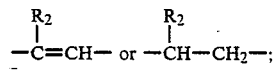

$R_1$ is selected from the group consisting essentially of hydrogen, alkyl($C_1$-$C_6$), —$CH_2CONH_2$, benzyl and

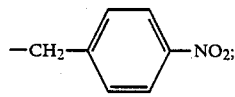

$R_2$ is selected from the group consisting essentially of

where $R_3$ and $R_4$ may be the same or different and may be selected from hydrogen, halogen, alkyl($C_1$-$C_3$), alkoxy($C_1$-$C_3$), nitro, morpholinyl and trifluoromethyl, $R_2$ may also be 3-pyridinyl; D—E may represent

where X is oxygen or sulfur or

where $R_5$ is lower alkyl($C_1$-$C_3$).

The present invention also includes novel compositions of matter containing the above-defined compounds which are useful as cognition enhancing agents, anxiolytic agents and/or antihypertensive agents in mammals and the methods for treating cognitive and related neural behavioral problems, anxiety and hypertension in mammals therewith.

This invention also includes the process for the chemical synthesis of the novel compounds disclosed herein.

DETAILED DESCRIPTION OF THE INVENTION

The novel compounds of the present invention are in general obtainable as white, yellow or tan crystalline solids having characteristic melting points and absorption spectra. They are generally soluble in organic solvents such as lower alkanols, acetonitrile, dichloromethane, dimethylsulfoxide, trifluoroacetic acid, N,N-dimethylformamide and the like, but are generally insoluble in water.

The novel substituted-6H,8H-pyrimido[1,2,3-cd]purine-8,10(9H)-diones and substituted-6H,10H-pyrimido[1,2-cd]purin-10-ones of the present invention may be readily prepared as set forth in the following reaction schemes:

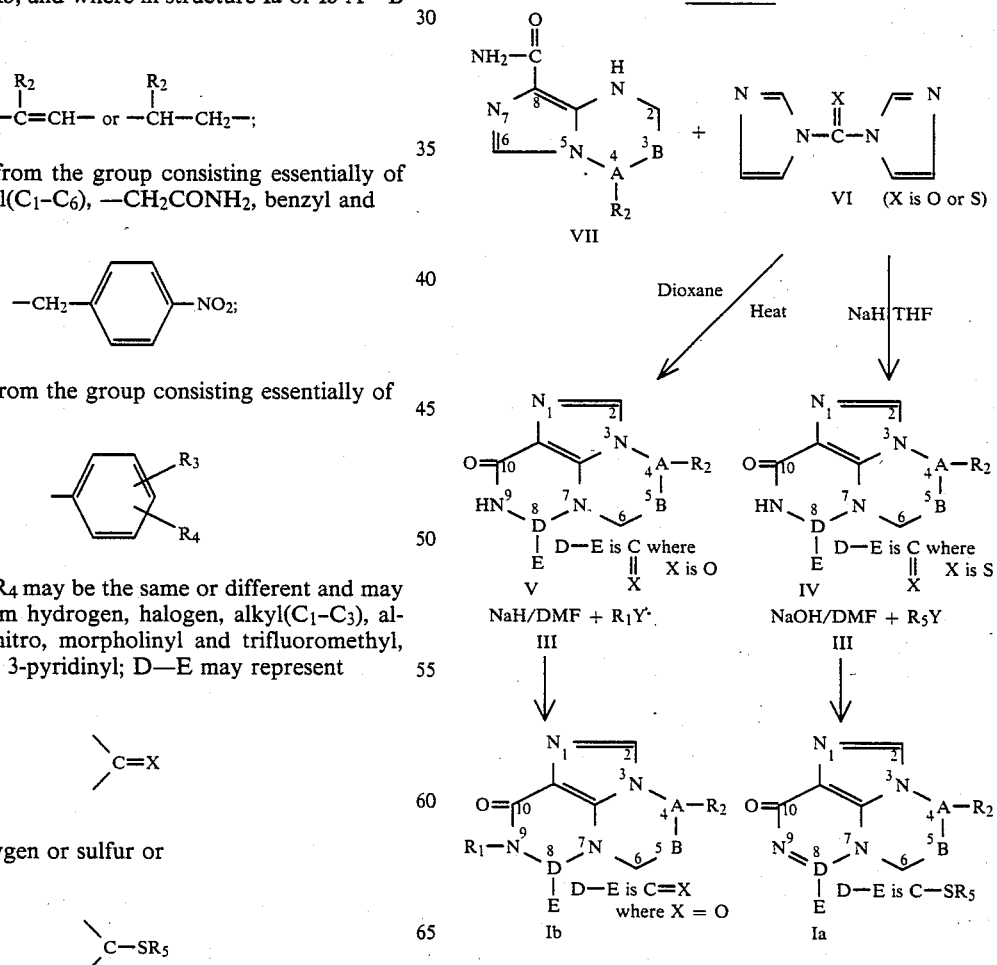

Scheme 1 wherein $R_1$, $R_2$, $R_3$, $R_4$, $R_5$, Ia, Ib, A—B, D—E and X are as hereinabove defined and Y is bromine or iodine.

As shown hereinabove (scheme 1) a substituted-1,2-dihydro or 1,2,3,4-tetrahydroimidazo[1,5-a]pyrimidine-8-carboxamide VII (prepared by the reduction of an imidazo[1,5-a]pyrimidine-8-carboxamide in the manner described in our Case 30,506) is reacted with 1,1-carbonyldiimidazole VI, (where X=oxygen) under nitrogen in an inert solvent such as p-dioxane and the like by heating at the reflux temperature for 4–96 hours to obtain the corresponding 4-substituted-6H,8H,primido[1,2,3-cd]purine-8,10(9H)-dione V, or the imidazo[1,5-a]pyrimidine-8-carboxamide VII, in an inert solvent such as dry tetrahydrofuran, cooled to −78° C. under nitrogen, is treated with sodium hydride (60% dispersion in mineral oil) and then reacted with 1,1′-thiocarbonyldiimidazole VI (where X=sulfur) by stirring for 2–3 hours at −78° C., then 36–48 hours while allowing the mixture to reach room temperature. The reaction mixture is quenched with water then neutralized to pH 6–7 with 5% hydrochloric acid to provide the 4-substituted-8-thioxo-6H,10H-pyrimido[1,2-cd]purin-10-one IV by crystallization or by extraction with an organic solvent such as chloroform and the like, and evaporation of the solvent.

The dione V may then be alkylated under nitrogen, at room temperature, in a solvent such as N,N-dimethylformamide and the like, using sodium hydride as the base, with an alkylating agent III, such as methyl iodide, iodoethane, 2-iodoacetamide, 4-nitrobenzyl bromide or benzyl bromide and the like for 6–60 hours. Evaporation of the solvent and treatment of the residue with water gives a solid, the solid may be purified by conventional means and recrystallized from solvents such as acetonitrile, ether, ethyl acetate and the like or combinations of solvents such as isopropyl alcohol/acetonitrile or ethyl alcohol/ethyl acetate and the like to give the corresponding substituted-6H,8H-pyrimido[1,2,3-cd]purine-8,10(9H)-dione, Ib.

When a 4-substituted-8-thioxo-6H,10H-pyrimido[1,2-cd]purin-10-one compound IV is suspended in a solvent such as N,N-dimethylformamide and the like, the mixture is made basic with 1N sodium hydroxide, and an alkylating agent such as methyl iodide or iodoethane and the like is added, with stirring at room temperature for 2–5 hours, the corresponding substituted-6H,10H-pyrimido[1,2-cd]purin-10-one, Ia is obtained as a precipitate, which is collected by filtration and washed with a solvent such as ether.

The 1,2-dihydroimidazo[1,5-a]pyrimidine-8-carboxamide intermediate compounds were in general prepared as follows: An imidazo[1,5-a]pyrimidine prepared as described in U.S. Pat. No. 4,236,005 with an election withdrawing carbamoyl group in the C8 position and a phenyl or substituted phenyl group in the C4 position is reacted with sodium cyanoborohydride by stirring in glacial acetic acid under nitrogen in an ice bath for approximately one hour, then at room temperature for from 1–48 hours. Evaporation of the solvent in vacuo provides a residue which is treated with water and filtered. The solid is dissolved in an inert solvent such as dichloromethane or acetonitrile and the like and is treated with saturated sodium bicarbonate solution, then washed with water. Separation and evaporation of the organic phase gives the crude dihydro product VII, which is recrystallized from a solvent such as ethanol, acetonitrile and the like or from a mixture of solvents such as ether-hexane, ethanol-methanol, chloroform-methanol, dichloromethane-hexane and the like.

Alternatively, as described in our Case 30,506, the 1,2-dihydroimidazo[1,5-a]pyrimidine-8-carboxamide intermediate compounds may be prepared by reacting an imidazo[1,5-a]pyrimidine-8-carboxamide (prepared as described in U.S. Pat. No. 4,236,005) with sodium borohydride pellets in a solvent such as methanol or tetrahydrofuran and the like, or a mixture of solvents such as methanol/tetrahydrofuran and the like by stirring under nitrogen at room temperature from 1–48 hours. Filtration and evaporation of the filtrate provides a residue which is washed with water, then is dissolved in an inert solvent such as dichloromethane or acetonitrile and the like, dried and purified by conventional means such as chromatography and crystallization.

The imidazo[1,5-a]pyrimidine intermediate compounds disclosed in U.S. Pat. No. 4,236,005 are prepared by condensation of an appropriately substituted 4-aminoimidazole with an appropriately substituted 3-dialkylaminoacrylophenone. The preferred procedure involves the reaction of the imidazole and the acrylophenone in refluxing glacial acetic acid in the presence of sodium acetate for a period of 2–24 hours.

The novel compounds of the present invention possess the ability to enhance neural function in warm-blooded animals affected by behavioral neurological problems, including the cognitive deterioration associated with decreased neural function which occurs with cerebral insufficiency, aging, dementia and similar conditions.

A useful in vivo test that measures how effectively central nervous system-acting drugs enhance survival in a hypoxic environment, presumably by improving the ratio of energy supply to demand is known as the Hypoxic Survival Test. This test demonstrates the ability of the test compounds relative to a known parasympathomimetic agent physostigmine. This test shows the enhanced survival of test animals in a hypoxic environment after treatment with drug as compared to saline treated control animals without drug. Extensive testing has demonstrated that under conditions of 10% oxygen, only 5–20% of control mice (treated with saline) survive after 5 minutes, whereas 60–80% of the physostigmine treated mice survive. Drugs are tested by intraperitoneally injecting groups of mice 30 minutes prior to placing them in a hypoxic mixture and measuring survival. The rationale of this test is that drugs which enhance survival under hypoxic conditions without concomitant, depression or sedative side effects, may do so by *enhancing* energy metabolism, or by *preserving* normal brain function under conditions of reduced energy metabolism. Given the dependence of the brain on a constant supply of energy, drugs which have this property may have many far-reaching therapeutic indications, including recovery from stroke and closed head injury, as well as reducing the deleterious effects of the aging central nervous system. For example, in aged and senile demented patients, energy metabolism is known to be deficient, and is thought to contribute significantly to the neurochemical and neurophysiological dysfunctions of aging.

Groups of 20 Royal Hart mice (6 weeks of age) are injected intraperitoneally with test compound (1–200 mg/kg) 30 minutes prior to placing them in a hypoxic mixture (10% oxygen in 90% carbon dioxide) and measuring survival after 5 minutes.

A separate group of 20 mice is injected intraperitoneally with saline solution (0.01 cc/g of body weight) and processed as described above.

Still another group of 20 mice is injected intraperitoneally with 0.125 mg/kg of physostigmine and processed as described above.

Results of this test on representative compounds of the present invention appear in Table I.

TABLE I

| Hypoxic Survival Test | | |
|---|---|---|
| Compound | Dose mg/kg | % Survivors |
| 4-(3-Nitrophenyl)-6H,8H—pyrimido[1,2,3-cd]purine-8,10(9H)—dione | 200 | 47 |
| 4-[4-(4-Morpholinyl)phenyl]-6H,8H—pyrimido[1,2,3-cd]purine-8,10(9H)—dione | 100 | 55 |

Another in vivo test associated with decreased neural function in mammals is the Passive Avoidance Anoxic Induced Amnesia Test. This test is used to determine the attenuation of anoxic induced amnesia in mice treated with drug, as compared to saline treated control animals with no drug.

A shock-motivated, single trial, step-through passive avoidance procedure is used. Groups of 25 Swiss-Webster, middle-aged mice (9 months of age) are placed singly in the front chamber of a 2-chamber box and are allowed to voluntarily cross into the rear chamber. As soon as the mouse enters the rear chamber, a door automatically traps the animal and a mild electric shock (0.4 mA for 4 seconds) is delivered to its feet. Following the foot shock, the mice are initially placed in an anoxic environment (0% oxygen) for 12 seconds, which quickly induces unconsciousness. They are then placed in an hypoxic environment (15% oxygen) for four minutes which prolongs the oxygen deprived state, maintaining unconsciousness. All testing is performed 24 hours later, and in all cases the mice appear fully recovered from the previous anoxic/hypoxic treatment. All test compounds are administered intraperitoneally at a dose of 10-200 mg/kg, 30 minutes prior to training and testing. Control animals are injected intraperitoneally only with saline at 0.01 cc/g of body weight.

The latency to enter the rear chamber is recorded for both training and testing. Presumably, the more the animal remembers being shocked, the greater it will inhibit going into the rear chamber and the higher will be its latency to re-enter. An improvement of 30% over saline control scores is considered active. The result of this test on a representative compound of the present invention appears in Table II.

TABLE II

| Passive Avoidance Anoxic Induced Amnesia Test | | |
|---|---|---|
| Compound | Dose mg/kg | % Improvement |
| 4-[3-(Trifluoromethyl)phenyl]-6H,8H—pyrimido[1,2,3-cd]purine-8,10(9H)—dione | 50<br>100 | 144<br>44 |
| 4-(3-Chlorophenyl)-6H,8H—pyrimido-[1,2,3-cd]purine-8,10(9H)—dione | 25<br>50 | 42<br>43 |
| 9-Methyl-4-[3-(trifluoromethyl)phenyl]-6H,8H—pyrimido[1,2,3-cd]purine-8,10(9H)—dione | 10<br>25<br>50<br>100 | 66<br>69<br>56<br>39 |
| 4-[4-(4-Morpholinyl)phenyl]-6H,8H—pyrimido[1,2,3-cd]purine-8,10(9H)—dione | 25 | 34 |

Certain of the novel compounds of the present invention possess central nervous system activity at non-toxic doses and as such may be useful as anxiolytic agents in that they produce certain responses in standard tests with laboratory animals which are known to correlate well with relief of anxiety in man. The compounds have been tested pharmacologically and have been found to have such properties with a desirable wide spread between doses producing anxiolytic activity and toxic symptoms.

A test utilized for the determination of anxiolytic activity is the measurement of the ability of test compounds to inhibit the binding of tritiated benzodiazepines to brain-specific receptors of warm-blooded animals. A modification of the method described by R. F. Squires, et al., Nature, 266, No. 21, pg 732 (Apr. 1977) and H. Mohler, et al., Science, 198, pg 849 (1977) was employed.

Male albino rats (Wistar strain, weighing 150-200 g each) were used. The test compounds were solubilized in either dimethylformamide, acetic acid, ethanol or hydrochloric acid.

Whole cortex of rats was homogenized gently in 20 volumes of ice-cold 0.32 M sucrose, centrifuged twice at 1000 g for 10 minutes and then recentrifuged at 30,000 g for 20 minutes to produce a crude $P_2$-synaptosomal fraction. The $P_2$-fraction was either: (1) resuspended in twice the original volume in hypotonic 50 mM Tris.HCl (pH 7.4), or (2) resuspended in one-half the original volume in hypotonic 10 mM Tris.HCl (pH 7.4) and frozen ($-20°$ C.) until time of use. Frozen $P_2$ preparations were thawed and resuspended in four times the original homogenizing volume at time of assay.

The binding assay consisted of 300 $\mu$l of the $P_2$-fraction suspension (0.2-0.4 mg protein), 100 $\mu$l of test drug and 100 $\mu$l of $^3$H-diazepam (1.5 nM, final concentration) or $^3$H-flunitrazepam (1.0 nM, final concentration) which was added to 1.5 ml of 50 mM Tris.HCl (pH 7.4). Non-specific binding controls and total binding controls received 100 $\mu$l of diazepam (3 $\mu$M final concentration) and 100 $\mu$l of deionized water, respectively, in place of the test compound. Incubation for 30 minutes proceeded in ice and was terminated by filtration, under vacuum, through glass fiber filters. The filters were washed twice with 5 ml of ice-cold 50 mM Tris.HCl (pH 7.4) and placed in scintillation vials. After drying at 50°-60° C. for 30 minutes, 10 ml of diluent was added and the radioactivity determined in a scintillation counter.

Inhibition of binding was calculated by the difference between total binding and binding in the presence of test compound, divided by the total binding, X 100. Physiological activity can be shown by a test compound that inhibits $^3$H-benzodiazepine binding by 12% or more. Such in vitro activity is biologically relevant when the test compound also demonstrates statistically significant anxiolytic activity through in vivo studies.

The results of this test on representative compounds of the present invention appear in Table III.

TABLE III

| Inhibition of the Binding of $^3$H—Benzodiazepine to Brain-Specific Receptors of Rats | |
|---|---|
| Compound | % Inhibition |
| 4-[3-(Trifluoromethyl)phenyl]-6H,8H—pyrimido[1,2,3-cd]purine-8,10(9H)—dione | 54 |
| 9-Ethyl-4-[3-(trifluoromethyl)phenyl]-6H,8H—pyrimido[1,2,3-cd]purine-8,10(9H)—dione | 17 |
| 8-(Methylthio)-4-phenyl-6H,10H—pyrimido-[1,2-cd]purin-10-one | 13 |

Certain of the novel compounds of the present invention are active hypotensive agents at non-toxic doses when administered to mammals. These compounds were tested for hypotensive activity by the method of P. S. Chan and D. Poorvin, Clinical and Experimental Hypertension, 1 (6), 817–830 (1979). Male, 16 week old, spontaneously hypertensive rats of the Okamoto strain having an average mean arterial blood pressure of 160+1.5 mm of mercury are used in the test. One to 3 rats are used per test compound. A rat is dosed by gavage with a test compound, suspended in 2% pre-boiled starch at a concentration of 50 mg/ml, at a dose of 100 mg/kg of body weight or less, with 0.9% sodium chloride loading at a dose of 25 ml/kg of body weight. A second identical dose of the test compound, without sodium chloride loading is given 24 hours later. At 28 hours after the initial dose the mean arterial blood pressure is measured by the method of Chan and Poorvin vide supra. The procedure is repeated in a second and third rat when necessary.

The results of this test on representative compounds of the present invention appear below in Table IV.

TABLE IV

| Reduction of Mean Arterial Blood Pressure in Spontaneously Hypertensive Rats | |
|---|---|
| Compound | MABP/mm Hg (No. of rats) |
| 4-(4-Methylphenyl)-6H,8H—pyrimido[1,2,3-cd]purine-8,10(9H)—dione | 127(1) |
| 4-(3-Pyridinyl)-6H,8H—pyrimido[1,2,3-cd]-purine-8,10(9H)—dione | 127(1) |
| 9-(Phenylmethyl)-4-[3-(trifluoromethyl)-phenyl]-6H,8H—pyrimido]1,2,3-cd]purine-8,10(9H)—dione | 132(2) |

The novel compounds of the present invention have been found to be useful as agents for the treatment of cognitive and related neural behavioral problems in mammals when administered in amounts ranging from about 5 mg to about 200 mg/kg of body weight per day. A preferred dosage regimen for optimum results would be from about 10 mg to about 50 mg/kg of body weight per day and such dosage units are employed that a total of from about 700 mg to about 3.5 g of the active compound for a subject of about 70 kg of body weight are administered in a 24 hours period.

Certain of the novel compounds of the present invention have been found to be useful for meliorating anxiety in mammals when administered in amounts ranging from about 0.5 mg to about 100 mg/kg of body weight per day. A preferred dosage regimen for optimum results would be from about 10 mg to about 50 mg/kg of body weight per day, and such dosage units are employed that a total of from about 700 mg to about 3.5 g of the active compound for a subject of about 70 kg of body weight are administered in a 24 hour period.

Certain of the novel compounds of the present invention have been found to be highly useful for lowering elevated blood pressure in mammals when administered in amounts ranging from about 2.0 mg to about 100 mg/kg of body weight per day. A preferred dosage regimen for optimum results would be from about 50 mg to about 750 mg per dose. Such dosage units are employed that a total of from about 200 mg to about 3.0 g of the active compound for a subject of about 70 kg of body weight are administered in a 24 hour period.

The hereinabove described dosage regimen for treating neural behavioral problems, meliorating anxiety and lowering elevated blood pressure in mammals may be adjusted to provide the optimum therapeutic response. For example, several divided doses may be administered daily or the dose may be proportionally reduced as indicated by the exigencies of the therapeutic situation. A decided practical advantage is that these active compounds may be administered in any convenient manner such as by the oral, intravenous, intramuscular or subcutaneous routes.

The active compounds may be administered orally, for example, with an inert diluent or with an assimilable edible carrier or they may be enclosed in hard or soft shell gelatin capsules, or they may be compressed into tablets or they may be incorporated directly with the food of the diet. For oral therapeutic administration, these active compounds may be incorporated with excipients and used in the form of tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained release preparations and formulations.

These active compounds may also be administered parenterally or intraperitoneally. Solutions or suspensions of these active compounds as a free base or pharmacologically acceptable salt can be prepared in water suitably mixed with a surfactant such as sodium lauryl sulfate or an emulsifier or stabilizer such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The invention will be described in greater detail in conjunction with the following non-limiting examples.

EXAMPLE 1

3-Dimethylaminoacrylophenone

A mixture of 50.0 g of acetophenone and 150 ml of N,N-dimethylformamide dimethyl acetal was stirred and heated at reflux for 8 hours. The mixture was allowed to cool to room temperature, then the solvent was removed in vacuo to give a crystalline residue. The residue was treated with 400 ml of hexane then filtered. The material on the filter was washed with hexane to give 47.8 g of the desired product as yellow crystals, mp 88°–91° C.

The following 3-(dimethylamino)acrylophenone intermediate compounds listed in Table V were prepared in a manner similar to the above procedure or by those described in U.S. Pat. Nos. 4,178,449; 4,236,005; 4,281,000; and 4,374,988.

TABLE V 3-(Dimethylamino)acrylophenone Intermediates $$R_2-\overset{O}{\underset{\|}{C}}-CH_3 + (CH_3O)_2-\overset{H}{\underset{|}{C}}-N-(CH_3)_2 \longrightarrow R_2-\overset{O}{\underset{\|}{C}}-CH=CHN(CH_3)_2$$

| Ex. | $R_2$ | Product | MP °C. |
|---|---|---|---|
| 2 | 3-Trifluoromethylphenyl | 3-Dimethylamino-3'-(trifluoromethyl)acrylophenone | 59–60 |
| 3 | 3-Chlorophenyl | 3'-Chloro-3-dimethylaminoacrylophenone | 68–70 |
| 4 | 2,5-Dichlorophenyl | 2',5'-Dichloro-3-dimethylaminoacrylophenone | 83–85 |
| 5 | 3-Methoxyphenyl | 3-Dimethylamino-3'methoxyacrylophenone | Viscous Liquid |
| 6 | 3,4 Dimethoxyphenyl | 3-Dimethylamino-3',4'-dimethoxyacrylophenone | 124–125 |
| 7 | 4-Chlorophenyl | 4'-Chloro-3-dimethylaminoacrylophenone | 83–84 |
| 8 | 4-Methoxyphenyl | 3-Dimethylamino-4'-methoxyacrylophenone | 92–95 |
| 9 | 3,4-Dichlorophenyl | 3',4'-Dichloro-3-dimethylaminoacrylophenone | 94–95 |
| 10 | 3-Nitrophenyl | 3-Dimethylamino-3'-nitroacrylophenone | 109–111 |
| 11 | 4-Methylphenyl | 3-Dimethylamino-4'-methylacrylophenone | 92.5–95 |
| 12 | 3-Pyridinyl | 3-Dimethylamino-1-(3-pyridinyl)-2-propen-1-one | 82–84 |
| 13 | 4-Morpholinophenyl | 3-Dimethylamino-4'-morpholinoacrylophenone | 209–211 |

EXAMPLE 14

4-(3-Chlorophenyl)imidazo[1,5-a]pyrimidine-8-carboxamide

A mixture of 13.9 g of 4-amino-5-imidazolecarboxamide hydrochloride, 24.0 g of 3'-chloro-3-dimethylaminoacrylophenone (U.S. Pat. No. 4,209,621, Ex. 50) and 200 ml of glacial acetic acid was heated at reflux for 5 hours. The liquid was evaporated in vacuo to give a yellow solid. The excess acid was neutralized with saturated sodium bicarbonate solution and this mixture was filtered and the solid was washed with water and then was dried. Recrystallization from ethanol-methanol gave 10.2 g of the desired product as yellow crystals, mp 252°–254° C.

EXAMPLE 15

4-(2,5-Dichlorophenyl)imidazo[1,5-a]pyrimidine-8-carboxamide

A stirred mixture of 5.2 g of 4-amino-5-imidazolecarboxamide hydrochloride and 10.0 g of 2',5'-dichloro-3-dimethylaminoacrylophenone (prepared as described in Example 4) in 80 ml of glacial acetic acid was heated at reflux for 4 hours. Evaporation in vacuo gave a dark oil which was dissolved in dichloromethane and treated with saturated sodium bicarbonate. The organic layer was separated, washed with water then dried over anhydrous sodium sulfate. The dichloromethane solution was passed through a short column of hydrous magnesium silicate. Evaporation of the eluate gave a semisolid which was treated with hot dichloromethane-hexane to give a yellow precipitate which was collected by filtration and dried to give 7.3 g of the product of the example, mp 230°–234° C.

EXAMPLE 16

4-Phenylimidazo[1,5-a]pyrimidine-8-carboxamide

A stirred mixture of 11.0 g of 4-amino-5-imidazolecarboxamide hydrochloride and 15.0 g of 3-dimethylaminoacrylophenone (prepared as described in Example 1) in 120 ml of glacial acetic acid was heated at reflux for 4 hours. The solvent was evaporated in vacuo to give a dark oil which was dissolved in dichloromethane, then treated by stirring with saturated sodium bicarbonate. The organic solvent was evaporated and the remaining mixture was filtered and the solid was washed with water, dried, and then was recrystallized from ethanol to give 7.08 g of the desired product as a yellow solid, mp 226°–228° C.

EXAMPLE 17

4-(3-Methoxyphenyl)imidazo[1,5-a]pyrimidine-8-carboxamide

A stirred mixture of 15.0 g of 3-dimethylamino-3'-methoxyacrylophenone (prepared as described in Example 5 and 9.2 g of 4-amino-5-imidazolecarboxamide hydrochloride in 150 ml of glacial acetic acid was heated at reflux for 24 hours. The solvent was evaporated in vacuo and the crystalline residue was treated with 100 ml of saturated sodium bicarbonate solution, filtered and washed with 200 ml of water to give yellow crystals. This material was treated with 400 ml of acetonitrile then with 600 ml of hot ethanol to give 9.9 g of the product of the example as yellow crystals, mp 249°–252° C.

EXAMPLE 18

4-(3,4-Dimethoxyphenyl)imidazo[1,5-a]pyrimidine-8-carboxamide

A stirred mixture of 15.0 g of 3-dimethylamino-3′,4′-dimethoxyacrylophenone (prepared as described in Example 6) and 8.0 g of 4-amino-5-imidazolecarboxamide hydrochloride in 150 ml of glacial acetic acid was heated at reflux for 24 hours. The solvent was evaporated in vacuo to give an oil. The oil solidified on standing at room temperature. The solid was treated with 200 ml of saturated sodium bicarbonate solution and then filtered to collect the crystals. The material was treated by boiling with 700 ml of ethanol and then was filtered. The solid was recrystallized from methanol-chloroform to give 7.9 g of the desired product, mp 262°–265° C.

EXAMPLE 19

4-(4-Chlorophenyl)imidazo[1,5-a]pyrimidine-8-carboxamide

A stirred mixture of 20.0 g of 4′-chloro-3-dimethylaminoacrylophenone (prepared as described in Example 7) and 12.0 g of 4-amino-5-imidazolecarboxamide hydrochloride in 450 ml of glacial acetic acid was heated at reflux for 6 hours. The mixture was allowed to stand at room temperature for 16 hours. The solvent was evaporated in vacuo and the crystalline residue was treated with saturated sodium bicarbonate and filtered and then it was washed with water. The crude product was then recrystallized from ethanol to give 17.0 g of yellow crystals. A 5.0 g amount of this material was heated on a steam bath in 300 ml of ethanol and 700 ml of chloroform, clarified hot with activated charcoal and filtered. The filtrate was evaporated in vacuo to give 4.3 g of the product of the example as yellow crystals, mp 290°–292° C.

EXAMPLE 20

4-(4-Methoxyphenyl)imidazo[1,5-a]pyrimidine-8-carboxamide

A stirred mixture of 15.0 g of 3-dimethylamino-4′-methoxyacrylophenone (prepared as described in Example 8) and 9.2 g of 4-amino-5-imidazolecarboxamide hydrochloride in 450 ml of glacial acetic acid was heated at reflux for 24 hours. Evaporation of the solvent in vacuo gave a solid which was treated with saturated sodium bicarbonate solution, then washed with water and filtered to give colorless crystals. This material was treated with hot acetonitrile and collected by filtration. Recrystallization from ethanol gave 6.1 g of the desired product as yellow crystals, mp 246°–249° C.

EXAMPLE 21

4-(3-Pyridinyl)imidazo[1,5-a]pyrimidine-8-carboxamide

A stirred mixture of 17.7 g of 3-dimethylamino-1-(3-pyridyl)-2-propen-1-one (U.S. Pat. No. 4,281,000, Ex. 1) and 12.6 g of 4-amino-5-imidazolecarboxamide hydrochloride in 100 ml of glacial acetic acid was heated on a steam bath for 4 hours. The reaction mixture was then allowed to stand at room temperature for 16 hours. The mixture was evaporated to dryness in vacuo and the residual solid was partitioned between dichloromethane and saturated sodium bicarbonate. The two layers were separated, the organic layer was dried over anhydrous sodium sulfate and filtered and evaporation of the filtrate gave a dark yellow solid which was treated with isopropyl alcohol. This solid was collected by filtration and washed with hexane. The yellow solid was dried in vacuo to give 10.0 g of the product of the example, mp >260° C.

EXAMPLE 22

4-(3,4-Dichlorophenyl)imidazo[1,5-a]pyrimidine-8-carboxamide

A stirred mixture of 12.0 g of 3′,4′-dichloro-3-dimethylaminoacrylophenone (prepared as described in Example 9) and 6.3 g of 4-amino-5-imidazolecarboxamide hydrochloride in 450 ml of glacial acetic acid was heated at reflux for 24 hours. The reaction mixture was allowed to stand at room temperature for 16 hours then the mixture was filtered and the crystals that were collected were washed with 300 ml of saturated sodium bicarbonate and then were washed with water. This material was dried, washed with hot methanol and filtered to give 5.9 g of the desired product as yellow crystals, mp 302°–304° C.

EXAMPLE 23

4-(3-Nitrophenyl)imidazo[1,5-a]pyrimidine-8-carboxamide

A stirred mixture of 18.0 g of 3-dimethylamino-3′-nitroacrylophenone (prepared as described in Example 10) and 10.30 g of 4-amino-5-imidazolecarboxamide hydrochloride in 450 ml of glacial acetic acid was heated at reflux for 24 hours. Upon standing at room temperature a crystalline precipitate was formed. The precipitate was collected, washed with saturated sodium bicarbonate solution and then with water to give 13.1 g of product. The material was recrystallized from methanol-chloroform by the addition of hexane and by scratching to give 8.7 g of the product of the example as yellow crystals, mp 282°–284° C.

EXAMPLE 24

4-(4-Methylphenyl)imidazo[1,5-a]pyrimidine-8-carboxamide

A mixture of 15.0 g of 3-dimethylamino-4′-methylacrylophenone (prepared as described in Example 11) and 10.0 g of 4-amino-5-imidazolecarboxamide hydrochloride in 150 ml of glacial acetic acid was stirred and heated at reflux for 4 hours. The mixture was evaporated in vacuo to give a yellow crystalline solid. The solid was treated with saturated sodium bicarbonate solution and was collected by filtration, and then it was recrystallized from acetonitrile to give 10.7 g of the desired product as yellow crystals, mp 263°–266° C.

EXAMPLE 25

4-[4-(4-Morpholinyl)phenyl]imidazo[1,5-a]pyrimidine-8-carboxamide

A mixture of 15.0 g of 3-dimethylamino-4′-morpholinoacrylophenone (prepared as described in Example 13) and 7.26 g of 4-amino-5-imidazolecarboxamide hydrochloride in 250 ml of glacial acetic acid was stirred and heated at reflux for 5 hours. The solution was evaporated in vacuo to give a black oil that was then dissolved in dichloromethane and then saturated sodium bicarbonate solution was added. A precipitate was formed which was collected by filtration as a yellow crystalline solid. The solid was triturated with ether then filtered to give 11.3 g of the product of the example as yellow crystals, mp 274°–277° C.

EXAMPLE 26

1,2-Dihydro-4-[3-(trifluoromethyl)phenyl]imidazo[1,5-a]pyrimidine-8-carboxamide To a solution of 9.2 g of 4-(α,α,α-trifluoro-m-tolyl)imidazo[1,5-a]pyrimidine-8-carboxamide (Ex. 28, U.S. Pat. No. 4,236,005) in 100 ml of glacial acetic acid, was added in portions 3.0 g of sodium cyanoborohydride at room temperature under nitrogen. The mixture was stirred at room temperature for 3 hours. The solvent was evaporated in vacuo to give an oil. The oil was triturated with water and a white precipitate formed, and this was collected by filtration, washed with water and then was slurried with saturated sodium bicarbonate solution. The precipitate was again collected by filtration and washed with water. This solid was dissolved in dichloromethane, and then water was added. The organic layer was separated, dried over anhydrous sodium sulfate and filtered. Evaporation of the filtrate gave a yellow solid which was recrystallized from acetonitrile to give 7.0 g of the product of the example as a light yellow solid, mp 192°–194° C.

EXAMPLE 27

4-(3-Chlorophenyl)-1,2-dihydroimidazo[1,5-a]pyrimidine-8-carboxamide

To a solution of 5.39 g of 4-(m-chlorophenyl)imidazo[1,5-a]pyrimidine-8-carboxamide (Example 14) in 100 ml of glacial acetic acid, was added in portions 2.8 g of sodium cyanoborohydride at room temperature under nitrogen. The mixture was stirred at room temperature for 2 hours. The solvent was evaporated in vacuo to give an oil, and this was dissolved in dichloromethane, then washed with saturated sodium bicarbonate solution. The organic layer was separated, dried over anhydrous sodium sulfate and filtered through a short column of hydrous magnesium silicate. Evaporation of the solvent gave a yellow solid which was recrystallized from acetonitrile to give 3.25 g of the desired product as a yellow solid, mp 182°–184° C.

EXAMPLE 28

4-(2,5-Dichlorophenyl)-1,2-dihydroimidazo[1,5-a]pyrimidine-8-carboxamide

To a solution of 4.0 g of 4-(2,5-dichlorophenyl)imidazo[1,5-a]pyrimidine-8-carboxamide (Example 15) in 80 ml of glacial acetic acid, was added in portions 1.8 g of sodium cyanoborohydride at room temperature, under nitrogen. The mixture was stirred at room temperature for 2 hours. The mixture was evaporated to dryness in vacuo and the residue was triturated with water to provide a white precipitate. The precipitate was collected and washed with water and the solid was dissolved in dichloromethane and extracted with saturated sodium bicarbonate solution. The layers were separated. The organic layer was dried over anhydrous sodium sulfate and filtered. Evaporation of the filtrate gave a yellow solid which was recrystallized from acetonitrile-ethanol to give 3.0 g of the product of the example as a light yellow solid, mp 190°–193° C.

Following the general procedure of Examples 26–28 and reacting the appropriate imidazo[1,5-a]pyrimidine derivative with sodium cyanoborohydride, the dihydro products of Examples 29–38, listed in Table VI, were obtained.

TABLE VI

| Ex. | Imidazo[1,5-a]pyrimidine Derivative | Dihydro- Product | MP °C. |
|---|---|---|---|
| 29 | 4-Phenylimidazo[1,5-a]pyrimidine-8-carboxamide | 1,2-Dihydro-4-phenylimidazo[1,5-a]pyrimidine-8-carboxamide | 152–154 |
| 30 | 4-(3-Methoxyphenyl)imidazo[1,5-a]pyrimidine-8-carboxamide | 1,2-Dihydro-4-(3-methoxyphenyl)imidazo[1,5-a]pyrimidine-8-carboxamide | 182–184 |
| 31 | 4-(3,4-Dimethoxyphenyl)imidazo[1,5-a]pyrimidine-8-carboxamide | 4-(3,4-Dimethoxyphenyl)-1,2-dihydroimidazo[1,5-a]pyrimidine-8-carboxamide | 276–280 |
| 32 | 4-(4-Chlorophenyl)imidazo[1,5-a]pyrimidine-8-carboxamide | 4-(4-Chlorophenyl)-1,2-dihydroimidazo[1,5-a]pyrimidine-8-carboxamide | 255–258 |
| 33 | 4-(4-Methoxyphenyl)imidazo[1,5-a]pyrimidine-8-carboxamide | 1,2-Dihydro-4-(4-methoxyphenyl)imidazo[1,5-a]pyrimidine-8-carboxamide | 236–240 |
| 34 | 4-(3,4-Dichlorophenyl)imidazo[1,5-a]pyrimidine-8-carboxamide | 4-(3,4-Dichlorophenyl)-1,2-dihydroimidazo[1,5-a]pyrimidine-8-carboxamide | 247–250 |
| 35 | 4-(3-Nitrophenyl)imidazo[1,5-a]pyrimidine-8-carboxamide | 1,2-Dihydro-4-(3-nitrophenyl)imidazo[1,5-a]pyrimidine-8-carboxamide | 208–210 |
| 36 | 4-(4-Methylphenyl)imidazo[1,5-a]pyrimidine-8-carboxamide | 1,2-Dihydro-4-(4-methylphenyl)imidazo[1,5-a]pyrimidine-8-carboxamide | 232–237 |
| 37 | 4-(3-Pyridinyl)imidazo[1,5-a]pyrimidine-8-carboxamide | 1,2-Dihydro-4-(3-pyridinyl)imidazo[1,5-a]pyrimidine-8-carboxamide | 190–193 |
| 38 | 4-[4-(4-Morpholinyl)phenyl]imidazo[1,5-a]pyrimidine-8-carboxamide | 1,2-Dihydro-4-[4-(4-morpholinyl)phenyl]imidazo[1,5-a]pyrimidine-8-carboxamide | 290–293 |

EXAMPLE 39

1,2-Dihydro-4-[3-(trifluoromethyl)phenyl]imidazo[1,5-a]pyrimidine-8-carbonitrile To a stirred mixture of 1.0 g of 4-(α,α,α-trifluoro-m-tolyl)imidazo[1,5-a]pyrimidine-8-carbonitrile (prepared as described in U.S. Pat. No. 4,236,005, Ex. 28) in 100 ml of methyl alcohol under nitrogen, at room temperature, was added, one at a time, 3 pellets of sodium borohydride, totaling about 300 mg. The mixture was stirred until the sodium borohydride was consumed and then was allowed to stand at room temperature. A precipitate which formed was filtered off and set aside (A). The filtrate was evaporated to dryness in vacuo. Water was added to the residue, then the mixture was extracted with dichloromethane. The organic solution was dried over anhydrous sodium sulfate then passed through a short column of hydrous magnesium silicate. Evaporation of the eluate with the addition of hexane gave crystals (B). The preceding precipitate (A) and the crystals (B) were combined and recrystallized from ethanol to give 350 mg of the product of the example as colorless crystals, mp 248°–250° C.

EXAMPLE 40

1,2,3,4-Tetrahydro-4-[3-trifluoromethyl)phenyl]imidazo[1,5-a]pyrimidine-8-carboxamide A 4.0 g amount of 1,2-dihydro-4-[3-trifluoromethyl)-]imidazo[1,5-a]pyrimidine-8-carboxamide with 1,1'-carbonyldiimidazole in dioxane or N,N-dimethylformamide and the like, at the reflux temperature for 4–96 hours gave the dione products of Examples 42–50, listed in Table VII.

TABLE VII

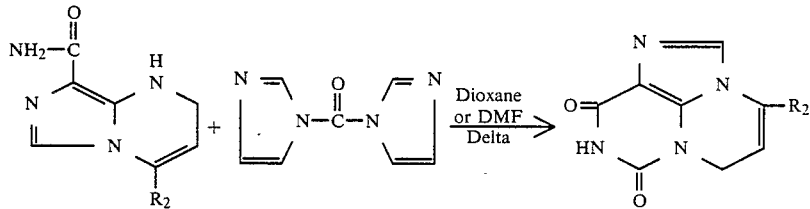

| Ex. | Dihydro Precursor | $R_2$ | Compound | MP °C. |
|---|---|---|---|---|
| 42 | Ex. 27 | 3-Chlorophenyl | 4-(3-Chlorophenyl)-6H,8H-pyrimido[1,2,3-cd]purine-8,10(9H)-dione | 291–294 |
| 43 | Ex. 28 | 2,5-Dichlorophenyl | 4-(2,5-Dichlorophenyl)-6H,8H-pyrimido[1,2,3-cd]purine-8,10(9H)-dione | 287–291 (dec.) |
| 44 | Ex. 29 | Phenyl | 4-Phenyl)-6H,8H-pyrimido[1,2,3-cd]purine-8,10(9H)-dione | 306–308 (dec.) |
| 45 | Ex. 30 | 3-Methoxyphenyl | 4-(3-Methoxyphenyl)-6H,8H-pyrimido[1,2,3-cd]purine-8,10(9H)-dione | 317–320 |
| 46 | Ex. 36 | 4-Methylphenyl | 4-(4-Methylphenyl)-6H,8H-pyrimido[1,2,3-cd]purine-8,10(9H)-dione | 311–314 |
| 47 | Ex. 35 | 3-Nitrophenyl | 4-(3-Nitrophenyl)-6H,8H-pyrimido[1,2,3-cd]purine-8,10(9H)-dione | >300 |
| 48 | Ex. 34 | 3,4-Dichlorophenyl | 4-(3,4-Dichlorophenyl)-6H,8H-pyrimido[1,2,3-cd]purine-8,10(9H)-dione | 335–338 |
| 49 | Ex. 37 | 3-Pyridinyl | 4-(3-Pyridinyl)-6H,8H-pyrimido[1,2,3-cd]purine-8,10(9H)-dione | 307–310 |
| 50 | Ex. 38 | (4-Morpholinyl)phenyl | 4-[4-(4-Morpholinylphenyl[-6H,8H-pyrimido-[1,2,3-cd]purine-8,10(9H)-dione | >300 | phenyl]imidazo[1,5-a]pyrimidine-8-carbonitrile (prepared as described in Example 39) in 80 ml of trifluoroacetic acid was heated to 55° C. in an oil bath, with stirring, under nitrogen then 9.0 ml of triethylsilane was added and the mixture was heated at 60°–65° C. for 10 hours. Stirring was continued for 16 hours at room temperature then the mixture was poured carefully into 160 ml of 25% aqueous potassium hydroxide. The solid that formed was collected by filtration and then was dissolved in 300 ml of chloroform. The organic solution was passed through a short column of hydrous magnesium silicate. The eluate was collected and set aside. The material remaining on the hydrous magnesium silicate was then extracted with acetonitrile and the extract was filtered and the filtrate was evaporated to give a semi-solid. This was treated with ether to give 1.2 g of a solid that was recrystallized from isopropyl alcohol to give the product of the example as a white solid, mp 179°–181° C.

EXAMPLE 41

4-[3-(Trifluoromethyl)phenyl]-6H,8H-pyrimido[1,2,3-cd]purine-8,10(9H)-dione

To a solution of 4.5 g of 1,2-dihydro-4-[3-trifluoromethyl)phenyl]imidazo[1,5-a]pyrimidine-8-carboxamide (Example 26) in 100 ml of dry dioxane, under nitrogen was added 10.0 g of 1,1'-carbonyldiimidazole. The mixture was heated at reflux for 22 hours. Evaporation of the reaction mixture gave a semi-solid which was treated with water to give a solid. The solid was recrystallized from acetonitrile/ethanol to give the product of the example as a white solid, mp 292°–295° C.

Following the general procedure of Example 41 and reacting the appropriate 1,2-dihydro-4-[substituted-

EXAMPLE 51

9-Methyl-4-[3-(trifluoromethyl)phenyl]-6H,8H-pyrimido[1,2,3-cd]purine-8,10(9H)-dione To a stirred suspension of 2.0 g of 4-[3-(trifluoromethyl)phenyl]-6H,8H-pyrimido[1,2,3-cd]purine-8,10-(9H)-dione (Example 41) in 20 ml of dry N,N-dimethylformamide was added 310 mg of sodium hydride (60% dispersion in mineral oil). The mixture was stirred at room temperature for 3 hours. To this mixture was added 2.0 ml of methyl iodide with continued stirring for 20 hours. The mixture was concentrated and the residue was treated with water to give a precipitate. The precipitate was collected by filtration, washed with water and dried to give 1.5 g of the desired product which was recrystallized from isopropyl alcohol/acetonitrile, as a white solid, mp 287°–290° C.

EXAMPLE 52

9-Ethyl-4-[3-(trifluoromethyl)phenyl]-6H,8H-pyrimido[1,2,3-cd]purine-6,10(9H)-dione To a stirred suspension of 3.0 g of 4-[3-(trifluoromethyl)phenyl]-6H,8H-pyrimido[1,2,3-cd]purine-8,10-(9H)-dione (prepared as described in Example 41) in 25 ml of dry N,N-dimethylformamide at room temperature, under nitrogen, was added 400 mg of sodium hydride (60% dispersion in mineral oil). The mixture was stirred for 2 hours, then 4 ml of iodoethane in 10 ml of dry N,N-dimethylformamide was added and the mixture was stirred for 20 hours. The mixture was evaporated to dryness in vacuo. The residue was treated with water to precipitate a yellow solid. The solid was collected, washed with water and dried to give 2.9 g of yellow solid. The solid was suspended in 20 ml of dry N,N-dimethylformamide and the procedure described hereinabove was repeated using 250 mg of sodium hydride and 4 ml of iodoethane with stirring for 20 hours. The reaction mixture was evaporated in vacuo to give an oil. The oil was treated with water to precipitate a solid. The solid was collected by filtration and dried in vacuo to give 3.20 g of the desired product which was recrystallized from ethanol/ethyl acetate, mp 278°–280° C.

EXAMPLE 53

8,10-Dioxo-4-[3-(trifluoromethyl)phenyl]-6H,8H-pyrimido[1,2,3-cd]purine-9(10H)-acetamide To a stirred suspension of 3.0 g of 4-[3-(trifluoromethyl)phenyl]-6H,8H-pyrimido[1,2,3-cd]purine-8,10-(9H)-dione (prepared as described in Example 41) in 30 ml of dry N,N-dimethylformamide at room temperature, under nitrogen was added 400 mg of sodium hydride (60% dispersion in mineral oil). The mixture was stirred for 2 hours then 2.0 g of 2-iodoacetamide was added and the mixture was stirred at room temperature for 16 hours. Evaporation of the mixture and treatment of the residue with water gave a white solid. The material was collected, washed with water and dried to give 3.10 g of solid. The solid was suspended and stirred in 20 ml of N,N-dimethylformamide and the procedure described hereinabove was repeated using 150 mg of sodium hydride and 500 mg of 2-iodoacetamide with stirring for 16 hours. The mixture was evaporated in vacuo to give a semi-solid which was treated with water to give a solid. The solid was collected by filtration and dried in vacuo to give 2.6 g of the desired product which was recrystallized from acetonitrile, mp 283°–285° C.

EXAMPLE 54

9-[(4-Nitrophenyl)methyl]-4-[3-(trifluoromethyl)phenyl]-6H,8H-pyrimido[1,2,3-cd]purine-8,10(9H)-dione To a stirred suspension of 5.0 g of 4-[3-(trifluoromethyl)phenyl]-6H,8H-pyrimido[1,2,3-cd]purine-8,10-(9H)-dione (prepared as described in Example 41) in 50 ml of dry N,N-dimethylformamide at room temperature, under nitrogen, was added 800 mg of sodium hydride (60% dispersion in mineral oil). The mixture was stirred for 2 hours, then 3.3 g of p-nitrobenzyl bromide in 10 ml of N,N-dimethylformamide was added and the mixture was stirred at room temperature for 40 hours. The mixture was evaporated to dryness, then was treated with water. The solid formed was collected by filtration, washed with water and dried in vacuo. The solid was stirred with 200 ml of dichloromethane and filtered. The filtrate was passed through a short column of magnesium silicate and the eluate was evaporated in vacuo to give 4.34 g of the product of the example which was recrystallized from isopropyl alcohol/acetonitrile as a white solid, mp 230°–232° C.

EXAMPLE 55

9-(Phenylmethyl)-4-[3-(trifluoromethyl)phenyl]-6H,8H-pyrimido[1,2,3-cd]purine-8,10(9H)-dione To a stirred suspension of 5.0 g of 4-[3-(trifluoromethyl)phenyl]-6H,8H-pyrimido[1,2,3-cd]purine-8,10-(9H)-dione (prepared as described in Example 41) in 50 ml of dry N,N-dimethylformamide at room temperature, under nitrogen, was added 800 mg of sodium hydride (60% dispersion in mineral oil). The mixture was stirred for 2 hours, then 3.1 g of benzyl bromide was added and the mixture was stirred at room temperature for 40 hours. The mixture was evaporated to dryness and treated with water to give a solid. The solid was collected and washed with water and dried. The solid was dissolved in chloroform and passed through a short column of magnesium silicate. The eluate was dried over anhydrous sodium sulfate and filtered. Evaporation of the filtrate gave an orange solid. The solid was triturated with diethyl ether, then filtered. The solid was washed with ether, then hexane and dried to give 4.0 g of the desired product which was recrystallized from ethyl acetate, mp 198°–200° C.

EXAMPLE 56

8,9-Dihydro-4-phenyl-8-thioxo-6H,10H-pyrimido-[1,2,3-cd]purine-10-one

To a stirred suspension of 1.0 g of 1,2-dihydro-4-phenylimidazo[1,5-a]pyrimidine-8-carboxamide (prepared as described in Example 29) in 30 ml of dry tetrahydrofuran cooled to −78° C. in a dry ice acetone bath was added in one portion 360 mg of sodium hydride (60% dispersion in mineral oil). The reaction mixture was stirred at −78° C. for 30 minutes then 817 mg of 1,1′-thiocarbonyldiimidazole was added in one portion and the mixture was stirred at −78° C. for 3 hours then allowed to warm slowly to room temperature and was stirred at room temperature for 36 hours. The reaction mixture was quenched with water and neutralized with 5% hydrochloric acid. The aqueous solution was extracted with chloroform. The organic layer was separated and evaporated in vacuo to give the product of the example as a yellow solid, mp 316°–317° C. (dec.).

EXAMPLE 57

8-(Methylthio)-4-phenyl-6H,10H-pyrimido[1,2-cd]-purin-10-one

To a suspension of 200 mg of 8,9-dihydro-4-phenyl-8-thioxo-6H,10H-pyrimido[1,2,3,-cd]purin-10-one (prepared as described in Example 56) in 5 ml of N,N-dimethylformamide was added 1.0 ml of 1N sodium hydroxide followed by 0.5 ml of methyl iodide. The reaction mixture was stirred for 3 hours at room temperature. The precipitate which formed was collected by filtration, washed with ether and dried to give 147 mg of the desired product as a white solid, mp 275°–277° C. (dec.).

EXAMPLE 58

4,5,8,9-Tetrahydro-4-[3-(trifluoromethyl)phenyl]-8-thioxo-6H,10H-pyrimido[1,2,3-cd]purin-10-one By the method of Example 56, 1,2,3,4-tetrahydro-4-[3-(trifluoromethyl)phenyl]imidazo[1,5-a]pyrimidine-8-carboxamide (Example 40) is reacted with sodium hydride and then 1,1′-thiocarbonyldiimidazole in tetrahydrofuran to give the title compound.

We claim:

1. Compounds of the formulae:

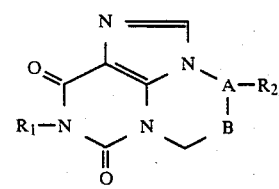
(I)

-continued

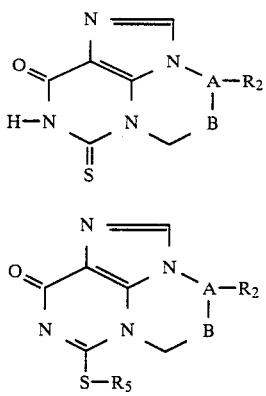

wherein the structure

may be

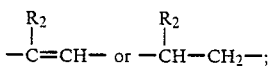

$R_1$ is hydrogen, alkyl($C_1$–$C_6$), carbamylmethyl, benzyl or p-nitrobenzyl; $R_2$ is 3-pyridinyl or a moiety of the formula:

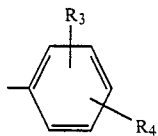

wherein $R_3$ and $R_4$ are each individually selected from the group consisting of hydrogen, halogen, alkyl(-$C_1$–$C_3$), nitro, alkoxy($C_1$–$C_3$), 4-morpholinyl and trifluoromethyl; and $R_5$ is alkyl($C_1$–$C_3$).

2. The compound according to claim 1, formula (I) thereof; 4-[3-(trifluoromethyl)phenyl]-6H,8H-pyrimido[1,2,3-cd]purine-8,10(9H)-dione.

3. The compound according to claim 1, formula (I) thereof; 4-(3-chlorophenyl)-6H,8H-pyrimido[1,2,3-cd]purine-8,10(9H)-dione.

4. The compound according to claim 1, formula (I) thereof; 9-methyl-4-[3-(trifluoromethyl)-phenyl]-6H,8H-pyrimido[1,2,3-cd]purine-8,10(9H)-dione.

5. The compound according to claim 1, formula (I) thereof; 4-(3-nitrophenyl)-6H,8H-pyrimido[1,2,3-cd]purine-8,10(9H)-dione.

6. The compound according to claim 1, formula (I) thereof; 4-(4-methylphenyl)-6H,8H-pyrimido[1,2,3-cd]purine-8,10(9H)-dione.

7. The compound according to claim 1, formula (I) thereof; 4-(3-pyridinyl)-6H,8H-pyrimido81,2,3-cd]purine-8,10(9H)-dione.

8. The compound according to claim 1, formula (I) thereof; 9-ethyl-4-[3-(trifluoromethyl)phenyl]-6H,8H-pyrimido[1,2,3-cd]purine,8,10(9H)-dione.

9. The compound according to claim 1, formula (I) thereof; 4-[4-(4-morpholinyl)phenyl]-6H,8H-pyrimido[1,2,3-cd]-purine-8,10(9H)-dione.

10. The compound according to claim 1, formula (I) thereof; 9-benzyl-4-[3-(trifluoromethyl)-phenyl]-6,8H-pyrimido[1,2,3-cd]purine-8,10(9H)-dione.

11. The compound according to claim 1, formula (II) thereof; 8,9-dihydro-4-phenyl-8-thioxo-6H,10H-pyrimido[1,2,3-cd]purine-10-one.

12. The compound according to claim 1, formula (III) thereof; 8-methylthio-4-phenyl-6H,10H-pyrimido[1,2-cd]purine-10-one.

13. A method of treating cognitive and related neural behavioral problems in warm-blooded animals which comprises administering internally to said warm-blooded animal an effective amount of a compound of claim 1.

14. A method of meliorating anxiety in a warm-blooded animal which comprises administering internally to said warm-blooded animal an effective anti-anxiety amount of a compound of claim 1.

15. A method of lowering elevated blood pressure in a mammal which comprises administering to said mammal an effective hypotensive amount of a compound of claim 1.

16. A cognitive enhancing composition of matter in dosage unit form comprising from about 50 mg to about 250 mg per dosage unit of a compound of claim 1 in association with a pharmaceutically acceptable carrier or diluent.

17. A therapeutic composition of matter in dosage unit form for the treatment of hypertension or anxiety which comprises 5 to 200 mg of a compound of claim 1 in association with a pharmaceutically acceptable carrier or diluent.

* * * * *